(12) United States Patent
Yi et al.

(10) Patent No.: US 8,157,718 B2
(45) Date of Patent: Apr. 17, 2012

(54) ELECTRIC CIRCUIT, HAVING TRANSFORMER WHICH CAN FUNCTION AS A BUFFER INDUCTOR, AND MAGNETIC STIMULATOR THEREWITH

(75) Inventors: Jeong-Han Yi, Seoul (KR); Jung-Hoe Kim, Seoul (KR); Soo-Yeol Lee, Gyeonggi-Do (KR); Min-Hyoung Cho, Gyeonggi-Do (KR)

(73) Assignee: MCube Technology Co., Ltd (KR)

( * ) Notice: Subject to any disclaimer, the term of this patent is extended or adjusted under 35 U.S.C. 154(b) by 989 days.

(21) Appl. No.: 11/792,022

(22) PCT Filed: Nov. 26, 2005

(86) PCT No.: PCT/KR2005/004007
§ 371 (c)(1),
(2), (4) Date: Jun. 2, 2008

(87) PCT Pub. No.: WO2006/057532
PCT Pub. Date: Jun. 1, 2006

(65) Prior Publication Data
US 2009/0105522 A1    Apr. 23, 2009

(30) Foreign Application Priority Data

Nov. 26, 2004  (KR) .................. 10-2004-0097838
Nov. 7, 2005   (KR) .................. 10-2005-0106142

(51) Int. Cl.
*A61N 1/00* (2006.01)

(52) U.S. Cl. .......................................... 600/13
(58) Field of Classification Search ............... 600/9–15; 363/27–28, 16–20, 21.01–26
See application file for complete search history.

(56) References Cited

U.S. PATENT DOCUMENTS

| | | | | |
|---|---|---|---|---|
| 5,880,944 A | * | 3/1999 | Hickman | 363/65 |
| 5,930,125 A | * | 7/1999 | Hitchcock et al. | 363/26 |
| 6,500,110 B1 | * | 12/2002 | Davey et al. | 600/13 |

* cited by examiner

*Primary Examiner* — John Lacyk
(74) *Attorney, Agent, or Firm* — The Farrell Law Firm, P.C.

(57) ABSTRACT

The present invention relates to an electric circuit having a transformer capable of functioning as a buffer inductor, and a magnetic stimulator using the transformer. The electric circuit of the present invention includes a power supply unit, and rectification means for rectifying current from the power supply unit. A transformer has an inductor on a primary side connected to the power supply unit. A capacitor is connected to an inductor on a secondary side of the transformer. Reverse flow prevention means is connected in series between the capacitor and the transformer to prevent charges stored in the capacitor from reversely flowing toward the transformer. A discharge inductor receives charges stored in the capacitor as discharge current and forms a magnetic field. First switching means turns on or off flow of the discharge current that flows in one direction. Bypass means causes current to flow in one direction.

37 Claims, 9 Drawing Sheets

ELECTRIC CIRCUIT, HAVING TRANSFORMER WHICH CAN FUNCTION AS A BUFFER INDUCTOR, AND MAGNETIC STIMULATOR THEREWITH

TECHNICAL FIELD

The present invention relates, in general, to magnetic stimulators for medical treatment and, more particularly, to a magnetic stimulator for medical treatment, in which a switching power transformer, which is a power supply unit, also functions as a current limiting inductor, and to an electric circuit for the magnetic stimulator.

BACKGROUND ART

A magnetic stimulator used for medical treatment is a non-contact type stimulator that remarkably reduces pain compared to an electric stimulator and generates current at the affected body part using a magnetic force generated near the affected body part. Accordingly, the magnetic stimulator has attracted attention as a device capable of stimulating the surface of the skin, or a region of the brain or spinal column into which an electrode cannot be easily inserted.

Such a magnetic stimulator basically includes a capacitor for storing energy necessary for stimulation and a coil for discharging the energy to form a strong magnetic field. That is, if a short and strong current is injected into the coil, a pulse-shaped magnetic field is formed, and this time-varying magnetic field causes an eddy current in the system of a human body, thus stimulating nerves using the same principles that current, injected through an electrode, stimulates nerves in an electric nerve stimulation method.

A representative example to which the magnetic stimulator is applied is a medical instrument for treating urinary incontinence. FIG. 1 is a view showing an example of a conventional non-contact type medical instrument for treating urinary incontinence.

A process for treating urinary incontinence is described in brief. A magnetic field generation device for generating a magnetic field is arranged below a chair-shaped medical instrument, and a pulse current generates a magnetic field in a core if the pulse current is supplied to a coil wound around the core while a patient sits down on the chair. This magnetic field forms a magnetic field closed loop between both ends of the core. The affected part of the patient is placed in the middle of the closed loop, so that an eddy current is induced again at the affected part due to the magnetic field, thus electrically stimulating the affected part.

FIG. 2 is a view showing a brain stimulator as another example to which the magnetic stimulator is applied. A magnetic field generation device 132 is placed on an affected region of the brain 130 of a patient, and the brain is stimulated using a magnetic field and an eddy current in the same principles as those of the above example.

In order to generate an eddy current having an intensity sufficient to cause the magnetic stimulator to exhibit a treatment effect, a magnetic field of several tesla must be generated in the form of a pulse having a width of several hundreds of micro seconds (μs).

FIG. 3 is a circuit diagram of the power supply circuit of a magnetic stimulator proposed previously by the present applicant, which shows a circuit capable of generating the magnetic field having the above-described intensity. Hereinafter, the operation of the circuit is described.

First, if an AC power supply unit provides typical Alternative Current (AC) power Vs, such as 110V to 220V, 50 Hz to 60 Hz, a transformer T boosts the AC power. Boosted current $I_4$ is full-wave rectified by a bridge diode B, and rectified current $I_1$ is charged in a capacitor through a resistor $R_1$ and a coil $L_1$. In this case, the resistor $R_1$ limits overcurrent of the current $I_1$ to protect related circuits, and the coil $L_1$ also functions to prevent overcurrent that may flow through circuits.

If the capacitor is charged to such an extent (+Vc) that the capacitor can be discharged, a switch S2 is turned on, thus starting discharging while causing high current $I_2$ to instantaneously flow through a discharge coil $L_2$. At the initial stage of discharging, when the voltage of the capacitor is +Vc, the current $I_2$ flows only through the discharge coil $L_2$, and current does not flow in the reverse direction $-I_1$ of the current $I_1$ because the current is interrupted by diodes, etc. The current $I_2$ flowing through the discharge coil $L_2$ is maximized when the voltage Vc of the capacitor is 0V. Thereafter, this energy is charged in the capacitor in the polarity −Vc opposite to the initial polarity.

During this discharging procedure, if the resistor $R_1$ and the coil $L_1$ do not exist, the discharge coil $L_2$ and the bridge diode form a single closed loop, so that the current $I_2$ is consumed as heat energy by respective devices and the resistance of a lead wire while flowing again through the discharge coil $L_2$ through the bridge diode and the switch S2, instead of charging the capacitor in the opposite polarity. In addition, since the current flowing at that time is overcurrent occurring when current charged in the capacitor flows at a time, serious damage to the input AC power source Vs is caused through the transformer T.

However, if a coil $L_1$ having a relatively high inductance exists in the circuit, a discharge frequency caused by the capacitor is very high, so that most current flowing through the above-described bridge diode and coil $L_1$ is interrupted, but is charged in the capacitor in the opposite polarity −Vc. Even in the case where a resistor $R_1$ having a relatively high resistance is used, the same effect can be obtained.

Thereafter, charges charged in the opposite polarity cause stimulation while passing again through the discharge coil $L_2$ as a reverse current $-I_2$. Even in this case, current $I_3$ from a branch node "a" to the transformer may be generated, but does not flow through the transformer due to the coil $L_1$ and/or the resistor $R_1$, because discharge frequency is very high. Most current flows through the discharge coil $L_2$ as a reverse current $-I_2$, and is used to form a magnetic field in the discharge coil $L_2$.

In the above circuit, the coil $L_1$ is an important and essential component. Further, as described above, this coil must have an inductance much higher than that of the discharge coil $L_2$ according to the characteristics thereof.

Because of the high inductance, the coil $L_1$ is actually manufactured to have a relatively large size of about 10 cm×10 cm×5 cm and have a weight of 1 kg or more, so that the coil $L_1$ is an obstruction to simplify the circuit.

Further, there is a problem that the manufacturing cost of a device greatly increases due to the coil $L_1$.

A more serious problem is that, as shown in the drawing, since the coil $L_1$ and/or the resistor $R_1$ are connected in series in a power charge path, part of power is always lost in the coil and the resistor at the time of charging power. Moreover, because power lost in this way is changed into heat, problems related to heat generation and cooling caused by the heat generation become serious.

Therefore, with respect to the essential coil and/or resistor, which increase manufacturing cost and cause power loss, the necessity for variously modifying and designing the coil or resistor has been recently required, and the present invention is developed to satisfy this necessity.

DISCLOSURE

Technical Problem

Accordingly, the present invention has been made keeping in mind the above problems, and an object of the present invention is to provide a new electric circuit, which is manufactured to allow an inductor on the secondary side of a transformer to function as a buffer inductor, so that there is no need to provide a separate buffer inductor, and the structure of a magnetic stimulator using the electric circuit.

Technical Solution

In order to accomplish the above object, the present invention provides an electric circuit, comprising a power supply unit; rectification means for rectifying current from the power supply unit; a transformer having an inductor on a primary side thereof connected to the power supply unit through the rectification means; a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof; reverse flow prevention means connected in series between the capacitor and the transformer to prevent charges stored in the capacitor from reversely flowing toward the transformer when the power is supplied; a discharge inductor for receiving the charges stored in the capacitor as discharge current and forming a magnetic field; first switching means for turning on or off flow of the discharge current that flows in one direction from the capacitor to the discharge inductor; and bypass means for causing current to flow in one direction from the discharge inductor to the capacitor, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and wherein the rectification means prevents a reverse current that may flow from the primary side inductor of the transformer to the power supply unit during L-C resonance.

Preferably, the electric circuit may further comprise second switching means connected in series between the power supply unit and the transformer. Preferably, the second switching means may be used as means for controlling on/off of a circuit on the primary side of the transformer when power is supplied in a fly-back mode or a forward mode, or used as means for preventing reverse current or overcurrent that may flow through the primary side of the transformer or the power supply unit.

Further, the present invention provides a magnetic stimulator, the magnetic stimulator comprising a power supply unit, a circuit unit supplied with power from the power supply unit to generate a magnetic field, and a control unit for controlling the circuit unit, the magnetic stimulator generating a magnetic field required for medical treatment, wherein the circuit unit comprises rectification means for rectifying current from the power supply unit; a transformer having an inductor on a primary side thereof connected to the power supply unit through the rectification means; a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof; reverse flow prevention means connected in series between the capacitor and the transformer to prevent charges stored in the capacitor from reversely flowing toward the transformer when the power is supplied; a discharge inductor for receiving the charges stored in the capacitor as discharge current and forming a magnetic field; first switching means for turning on or off flow of the discharge current that flows in one direction from the capacitor to the discharge inductor; and bypass means for causing current to flow in one direction from the discharge inductor to the capacitor, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, wherein the rectification means prevents a reverse current that may flow from the primary side inductor of the transformer to the power supply unit during L-C resonance, and wherein if a magnetic field is generated in the discharge inductor by the L-C resonance, the magnetic field is penetrated into an affected part of a patient, thus generating an induced current in the affected part. Preferably, the magnetic stimulator may further comprise second switching means connected in series between the power supply unit and the transformer.

Further, the present invention provides an electric circuit, comprising a power supply unit; rectification means for rectifying current from the power supply unit; a transformer having an inductor on a primary side thereof connected to the power supply unit through the rectification means; a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof; reverse flow prevention means connected in series between the capacitor and the transformer to prevent charges stored in the capacitor from reversely flowing toward the transformer when the power is supplied; a discharge inductor for receiving the charges stored in the capacitor as discharge current and forming a magnetic field; first switching means for turning on or off flow of the discharge current that flows in one direction from the capacitor to the discharge inductor; bypass means for causing current to flow in one direction from the discharge inductor to the capacitor; and second switching means connected in series between the power supply unit and the transformer, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and wherein the second switching means controls on/off of a path connected from the primary side inductor of the transformer to the power supply unit so that power can be supplied in a fly-back mode when the power supply unit supplies power to the capacitor, and wherein the rectification means prevents a reverse current that may flow from the primary side inductor of the transformer to the power supply unit during L-C resonance.

Further, the present invention provides a magnetic stimulator, the magnetic stimulator comprising a power supply unit, a circuit unit supplied with power from the power supply unit to generate a magnetic field, and a control unit for controlling the circuit unit, the magnetic stimulator generating a magnetic field required for medical treatment, wherein the circuit unit comprises rectification means for rectifying current from the power supply unit; a transformer having an inductor on a primary side thereof connected to the power supply unit through the rectification means; a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof; reverse flow prevention means connected in series between the capacitor and the transformer to prevent charges stored in the capacitor from reversely flowing toward the transformer when the power is supplied; a discharge inductor for receiving the charges stored in the capacitor as discharge current and forming a magnetic field; first switching means for turning on or off flow of the discharge current that flows in one direction from the capacitor to the discharge inductor; bypass means for causing current to flow in one direction from the discharge inductor to the capacitor; and second switching means connected in series between the power supply unit and the transformer, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and wherein the second switching means controls on/off of a path connected from the primary side inductor of the transformer to the power supply unit so that power can be supplied in a fly-back mode when the power supply unit supplies power to the capacitor, wherein the rectification means prevents a reverse current that may flow from the primary side inductor of the transformer to the power supply unit during L-C resonance, and wherein if a magnetic field is generated in the discharge inductor by the L-C resonance, the magnetic field is penetrated into an affected part of a patient, thus generating an induced current in the affected part.

Further, the present invention provides an electric circuit, comprising a power supply unit; a transformer having an inductor on a primary side thereof connected to the power supply unit; a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof; rectification/reverse flow prevention means connected in series between the capacitor and the transformer to simultaneously supply Direct Current (DC) current to the capacitor and prevent charges stored in the capacitor from reversely flowing toward the transformer when the power is supplied; a discharge inductor for receiving the charges stored in the capacitor as discharge current and forming a magnetic field; first switching means for turning on or off flow of the discharge current that flows from the capacitor to the discharge inductor; bypass means for causing current to flow in one direction from the discharge inductor to the capacitor; and second switching means connected in series between the power supply unit and the transformer, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and wherein the second switching means controls on/off of a path connected from the primary side inductor of the transformer to the power supply unit so that power can be supplied in a fly-back mode when the power supply unit supplies power to the capacitor, and, in addition, the second switching means is turned off during L-C resonance to prevent a reverse current that may flow from the primary side inductor of the transformer to the power supply unit, and a magnetic stimulator using the electric circuit.

Advantageous Effects

The present invention relates to a magnetic stimulator and an electric circuit thereof, and is characterized in that an inductor on the secondary side of a power supply transformer also functions as a buffer inductor.

Therefore, the magnetic stimulator of the present invention is advantageous in that, since there is no need to provide a separate buffer inductor compared to a conventional magnetic stimulator, a heat problem or power loss problem occurring due to the inductor can be eliminated, and, in addition, the circuit part of the stimulator can be simplified and production cost thereof can be reduced.

BEST MODE

Figure 1:
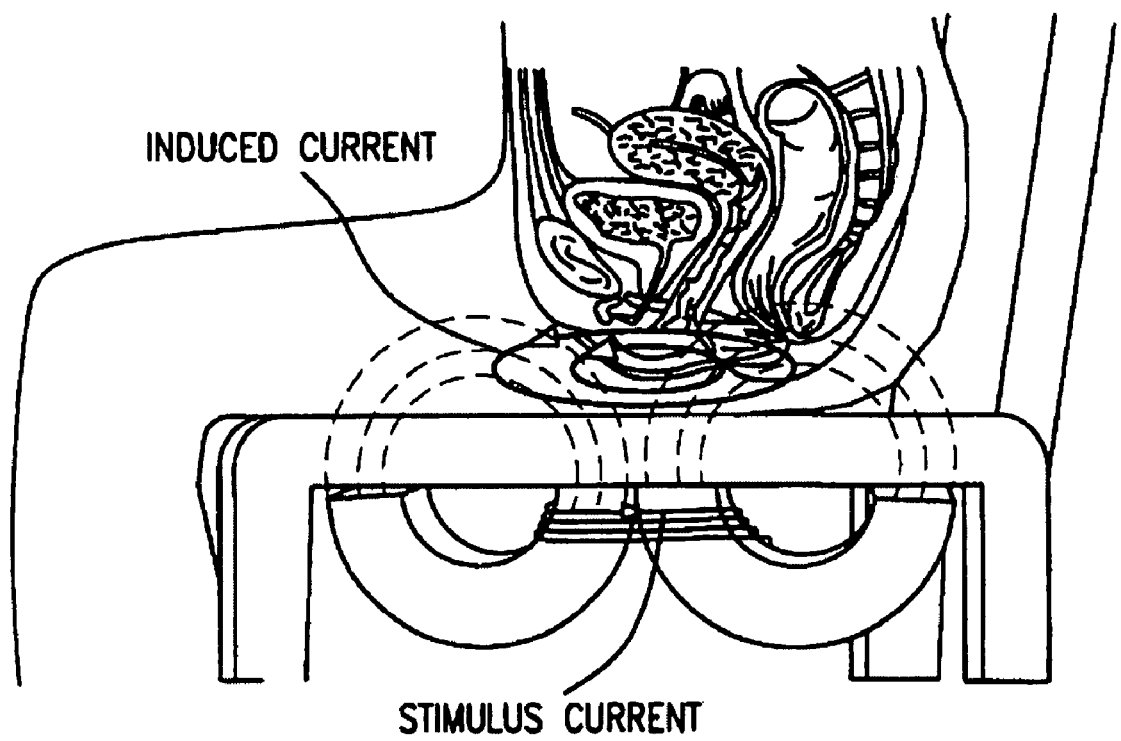
FIG. 1 is a view showing a magnetic stimulator used for a medical instrument for treating urinary incontinence.
Figure 2:
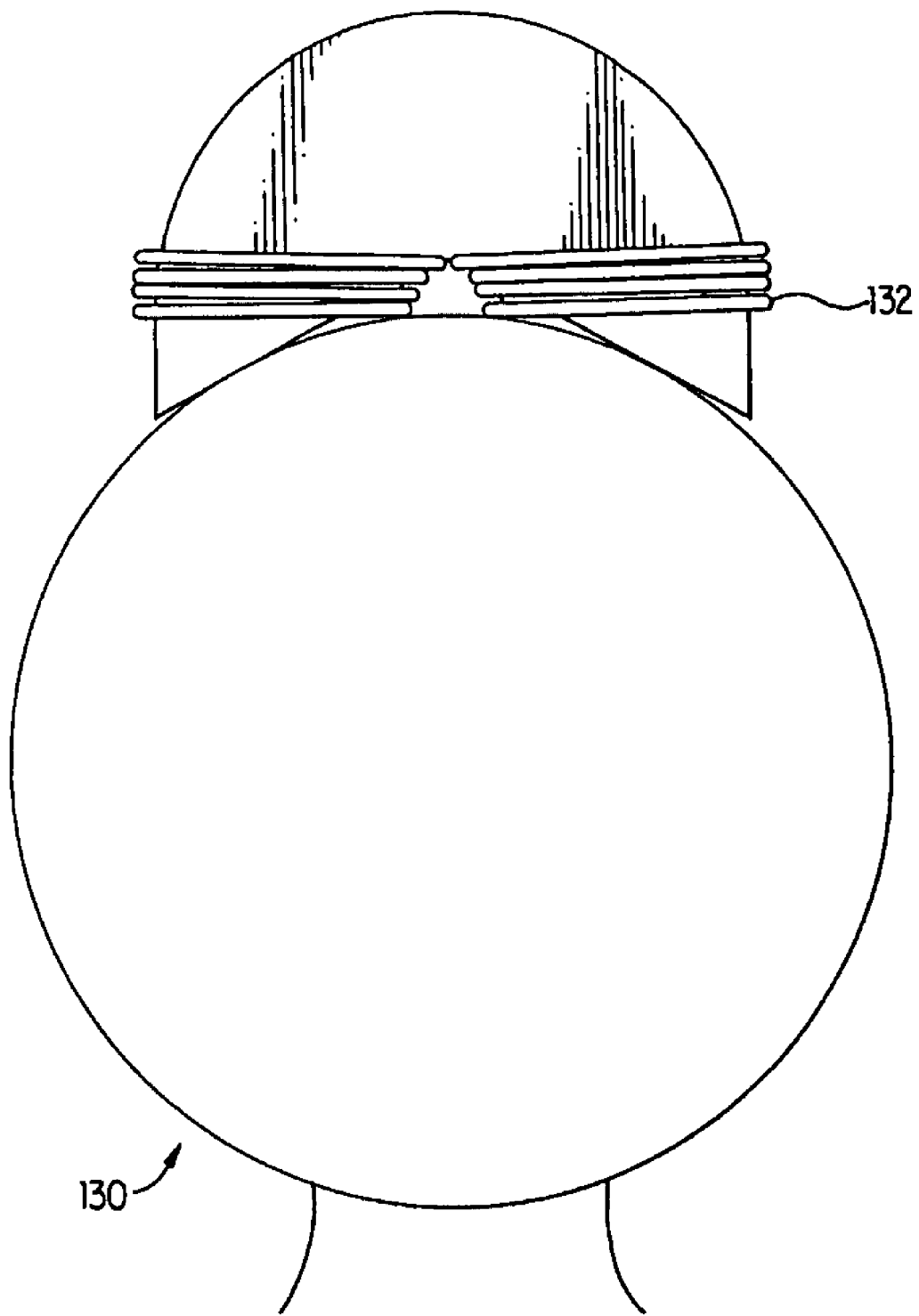
FIG. 2 is a view showing a magnetic stimulator used as a brain stimulator.

Reference should now be made to the drawings, in which the same reference numerals are used throughout the different drawings to designate the same or similar components.

Figure 4:
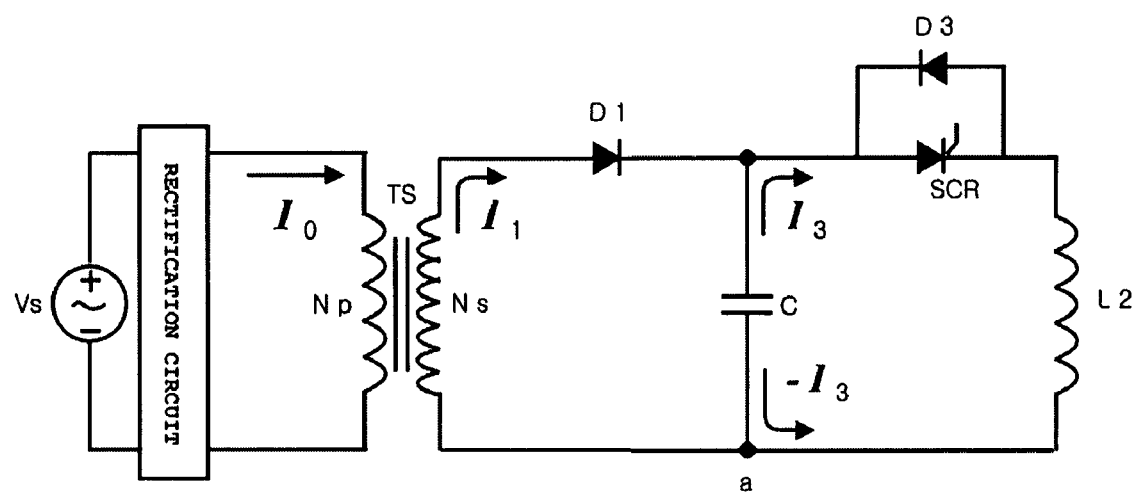
FIG. 4 is a circuit diagram showing an embodiment of the present invention in which only a rectification circuit exists on the primary side of a transformer.

FIG. 4 is a circuit diagram of a basic embodiment of the present invention, which shows a circuit diagram of a magnetic stimulator according to the present invention, which is manufactured to integrate a buffer inductor with an inductor on the secondary side of a transformer, or constructed to allow the inductor on the secondary side of the transformer to function as a buffer inductor.

On the primary side (Np) of a power supply unit, that is, a transformer, placed on the left side of the circuit, an AC power source (Vs) for supplying power to an entire circuit system, a rectification circuit for full-wave rectifying or half-wave rectifying AC current supplied by the AC power source, and the transformer TS for supplying power to a capacitor while transforming a voltage, are provided.

On the secondary side (Ns) of the transformer, a capacitor C for supplying power to a discharge inductor L2 is arranged, and a diode $D_1$, which is an example of a means for preventing stored charges from reversely flowing toward the transformer at the time of supplying current to the capacitor C, is disposed between the transformer and the capacitor C. For this reverse flow prevention means, any type of device capable of performing a reverse flow prevention function can be used in addition to the diode.

On the right side of the capacitor C, the discharge inductor L2 for causing L-C resonation together with the capacitor using current and generating a magnetic stimulation pulse is connected through a Silicon Controlled Rectifier (SCR) and a bypass diode D3 for providing a resonance path.

The SCR functions as a switch for switching on/off between the capacitor and the discharge inductor L2.

The important fact of the circuit is that the coil ($L_1$, hereinafter referred to as a buffer inductor) and/or a resistor ($R_1$, hereinafter referred to as a buffer resistor) of FIG. 3, which may cause a problem, physically do not exist. Therefore, the circuit has an advantage in that problems caused by the coil and the resistor do not fundamentally occur, but a method of implementing the essential function of the conventional coil and resistor, that is, the function of charging the capacitor in L-C resonance and limiting overcurrent flowing through the primary side of a transformer may be an issue. In relation to this issue, the operating waveform of the circuit is described first, and the solving method thereof is described later.

Figure 5:
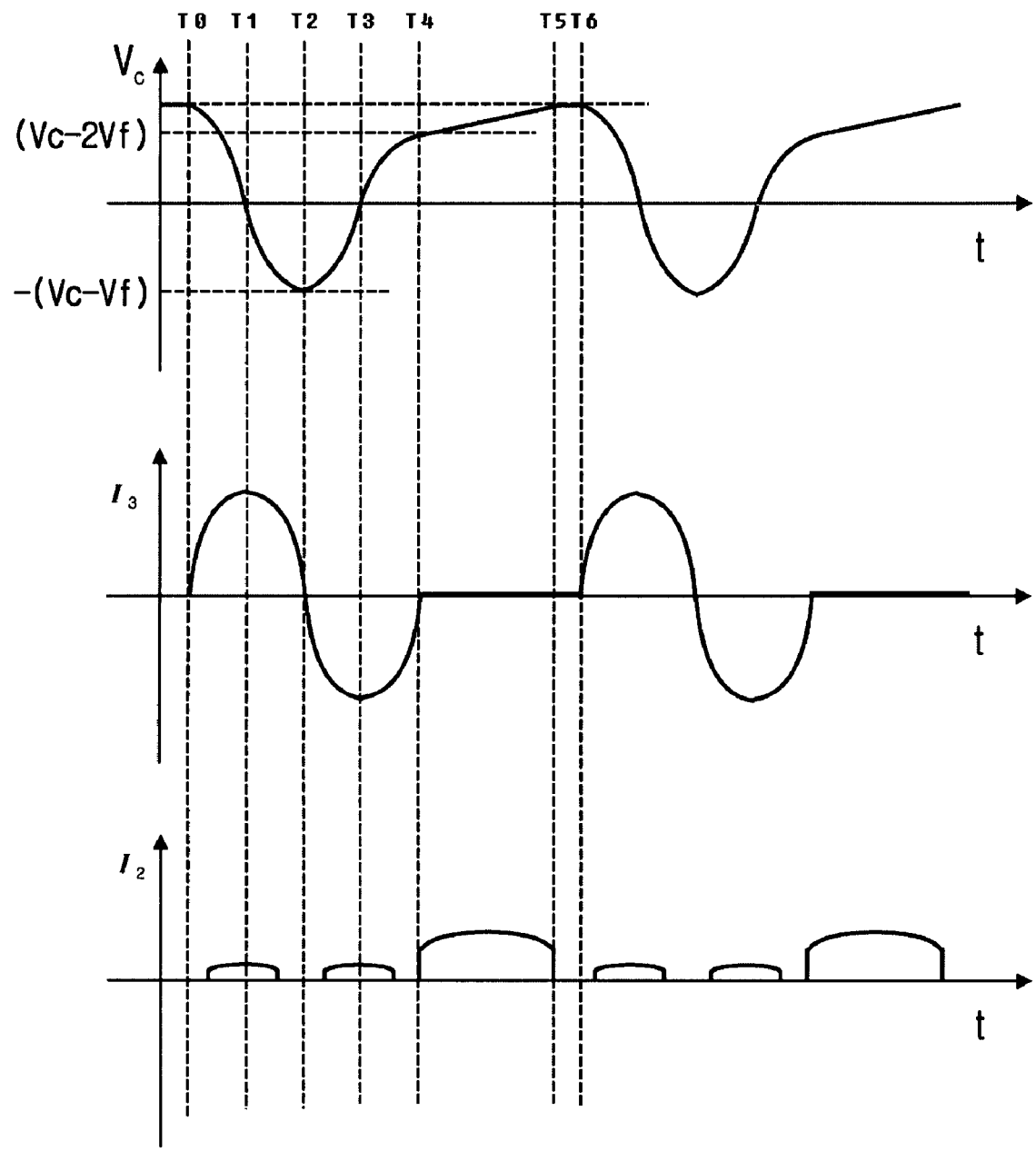
FIG. 5 is an operating waveform diagram of FIG. 4.

FIG. 5 is a diagram showing the operating waveform of FIG. 4.

First, variation in the voltage Vc of the capacitor is described. Current is supplied to the capacitor through the power source Vs, the rectification circuit and the transformer until voltage is charged in the capacitor to Vc before time T0, which is an initial state.

At time T0 when the sufficient discharge voltage Vc is stored, if the SCR, a switching means which interrupted the discharging of the capacitor, is turned on, charges stored in the capacitor are suddenly discharged, and current $I_3$, increasing in the form of a sine wave, is generated and is supplied to the discharge inductor L2. The current $I_3$ generates an initial pulse magnetic field in the discharge inductor L2.

As time elapses, the intensity of the current $I_3$ increases, and then decreases from a peak point appearing at time T1 at which the voltage of the capacitor is 0. Further, the current $I_3$, having passed through the discharge inductor L2, circulates through a loop and starts to charge the capacitor C in a polarity opposite to the initial polarity.

The current $I_3$ charges the capacitor in the polarity opposite to the initial polarity while passing through the discharge inductor L2 until time reaches T2. Next, after T2, current generates a pulse magnetic field in the discharge inductor L2 once again while flowing in the direction of $-I_3$, which is opposite to the initial direction. Thereafter, the current starts to recharge the capacitor in the same polarity as the initial polarity. Such a phenomenon continues up to time T4 at which charges stored in the capacitor C are completely discharged and move to the opposite side.

The maximal voltage of the capacitor recharged in the initial polarity becomes Vc−2Vf, that is, a value decreasing from Vc by a value consumed during the generation of the pulse magnetic field twice if another resistance in a lead wire is ignored.

Therefore, the step of compensating for decreased power of the capacitor from the power source Vs during the interval between T4 and T5 is performed so as to perform a subsequent discharging cycle. At this loss compensating step, a switching device on the primary side of the transformer is turned on to cause rectified current $I_0$ to flow and induce $I_1$ from the current $I_0$, thus charging the capacitor. Further, as a charging method used in this step, either a forward mode or a fly-back mode can be used.

If the voltage of the capacitor is charged up to Vc after time T5, the SCR is turned on at time T6 after the system has been stabilized if necessary, and the above-described discharging cycle is repeated.

Figure 3:
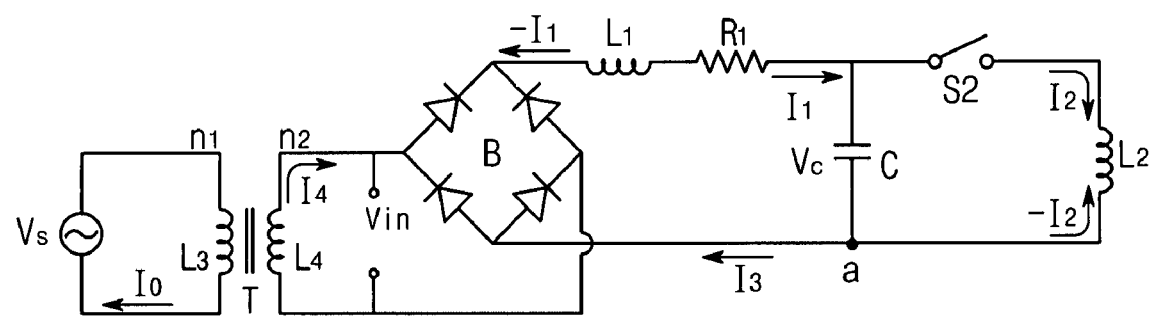
FIG. 3 is a circuit diagram of a conventional magnetic stimulator.

Following common sense, since the circuit of FIG. 4 is not provided with a buffer inductor or a buffer resistor, unlike the circuit of FIG. 3, it may be preferable that the current $I_3$, flowing through a branch node "a" during the interval ranging from time T2 to T4, become current $I_1$ flowing through the secondary side of the transformer rather than the capacitor, and be consumed as heat while circulating between the transformer and the discharge inductor L2.

However, the circuit of the present invention of FIG. 4 is constructed to cause the inductor on the secondary side (Ns) of the transformer to have an inductance 10 to 1000 times higher than that of the discharge inductor L2. Accordingly, the circuit is constructed so that most current $I_3$, passing through the branch node "a" during the interval ranging from time T2 to time T4, can flow through the capacitor and can be used to charge the capacitor in the opposite polarity. Due to this construction, there is no need to use a conventional buffer inductor or buffer resistor.

Further, as shown in FIG. 5, even though the two inductors have a high inductance difference therebetween, part of $I_3$ flows as $I_1$ at the branch node "a" during the interval between the time T1 and time T3. As described above, this current $I_1$ can generate, on the primary side of the transformer, an induced electromotive force, sufficient to destroy the power source Vs or apply at least a strong electric shock to the power source, and overcurrent or reverse current $-I_0$, caused by the induced electromotive force, while flowing through the secondary side of the transformer.

However, in the circuit on the primary side of the transformer of FIG. 4, the rectification circuit is provided, and current is set to flow only in the direction of $I_0$, so that the reverse current $-I_0$ cannot flow, as far as breakdown or dielectric breakdown does not occur in parts constituting the rectification circuit, for example, diodes, thus solving the problem.

The core technical feature of the embodiment of the present invention resides in the fact that the embodiment is constructed to eliminate a buffer inductor and/or a buffer resistor, which were essential components in the prior art, from the magnetic stimulator circuit, and instead allow the inductor on the secondary side of the transformer to perform a buffering function, and is constructed to provide a rectification means on the primary side of the transformer to safely protect power.

If the circuit of the present invention is analyzed, it is difficult to consider that the conventional buffer inductor $L_1$ used in the circuit of FIG. 3 is eliminated from the circuit of the present invention, but it is more preferable to consider that the buffer inductor is physically integrated with the inductor on the secondary side (Ns) of the transformer, because the inductor on the secondary side clearly temporally separates and performs two functions.

That is, in the interval ranging from time T4 to T5, during which the power supply unit supplies power to the capacitor, the inductor on the secondary side functions as the secondary side of the transformer for supplying lost power to the capacitor. In contrast, in the interval ranging from time T0 to T4, during which the capacitor causes L-C resonance while being discharged, the inductor on the secondary side clearly functions only as a buffer inductor.

Therefore, the two functions temporally separated in this way are physically implemented in a single inductor, so that the magnetic stimulator of the present invention has a compact and efficient circuit compared to the conventional magnetic stimulator.

In order for the secondary side inductor of the transformer to function as a buffer inductor in addition to the secondary side function of the transformer, the following conditions must be preferably satisfied.

First, the inductance of the secondary side inductor must be relatively higher than that of the inductor L2, as described above. This definition is required to cause the intensity of the current $I_1$ to be as low as possible when the capacitor is discharged in the opposite polarity, as described above.

As an example of the ratio of inductance of the secondary side inductor of the transformer to the inductance of the inductor L2, if the maximal charged voltage of a capacitor having a capacitance of 50 μF is 1000V and the inductance of the inductor L2 is 100 μH, the secondary side inductor of the transformer may have an inductance of about 1 mH, which is ten times that of the inductor L2.

However, such an inductance ratio is only an example for estimating intensity; and can be freely varied depending on the purpose of a system to be used and the capacity of other devices.

Further, if the secondary side inductor of the transformer has a core, it is preferable that the saturation magnetic value of the core be higher. The reason for this is that, if the saturation magnetic value of the core constituting the inductor is low, there may occur a problem in that the core is saturated by current $I_1$ and the secondary side path of the transformer is shorted, so that the above-described buffering effect no longer occurs.

Therefore, as the core of the secondary side inductor of the transformer, a material, having a saturation value sufficient to prevent the core from being saturated by current flowing through the secondary side of the transformer when the capacitor is discharged, can be used. Generally, a ferrite series material or a multi-layered silicon steel sheet can be used as the core.

However, if the inductance of an inductor itself is sufficiently high even though the inductor does not have a core, the same effect can be obtained. Accordingly, an embodiment lacking a core is not excluded from the embodiments of the present invention.

In the circuit of FIG. 4, overcurrent may flow through the primary side of the transformer because a resistor does not exist on the primary side of the transformer in the drawing, or only a very low conductor resistance exists. If a constant voltage source (Vs) is used as a power supply unit, there is the risk of infinitely increasing DC current rectified by a rectification circuit. That is, even though such a DC current cannot actually be an infinite value, the DC current may increase to such an extent as to destroy the transformer, so that a means for preventing the increase of the DC current may be required.

Figure 6:
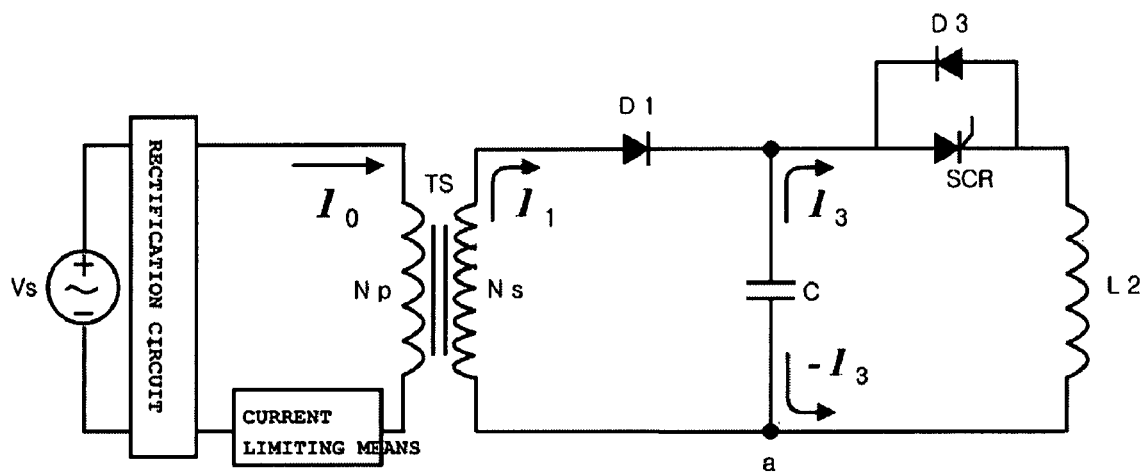
FIG. 6 is a circuit diagram showing an embodiment of the present invention in which a current limiting means exists on the primary side of a transformer.

In order to prevent such a phenomenon, a current limiting means can be additionally provided on the primary side of the transformer, as shown in FIG. 6. As described above, the function of the current limiting means is to prevent infinite current from flowing. In detail, the current limiting means is implemented using a resistor having a suitable resistance or using a switch, thus turning off the circuit if current higher than a certain intensity is flowing.

Since the current limiting means may be additionally attached when there is a risk of causing overcurrent, it is not an essential component necessary for the present invention. Further, when a switching device, etc. are provided on the primary side of the transformer to supply power in a fly-back mode, the switching device can also function as a current limiting means without separately providing the current limiting means.

MODE FOR INVENTION

Figure 7:
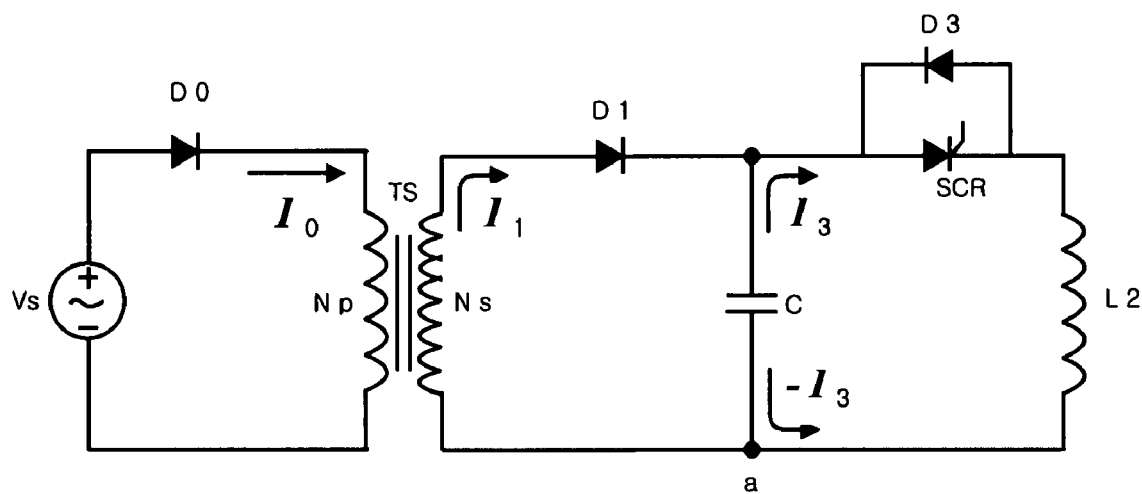
FIGS. 7 and 8 are circuit diagrams showing circuits of the present invention, in which a half-wave rectification means and a full-wave rectification means are included as a rectification means, respectively, in the embodiment of FIG. 4.
Figure 8:
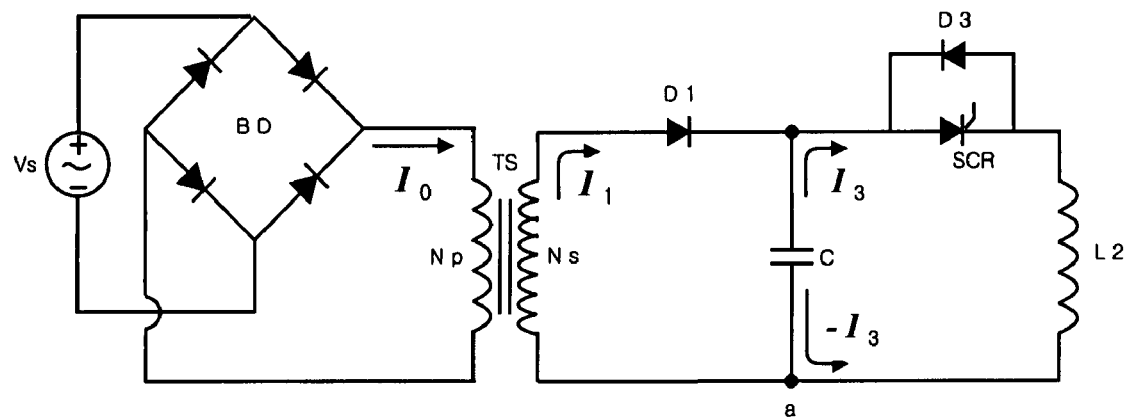

FIGS. 7 and 8 are circuit diagrams showing the rectification circuit of FIG. 4 in detail according to other embodiments of the present invention.

In FIG. 7, an embodiment, in which current $I_0$, half-wave rectified by a diode D0 connected in series between a power source and the primary side of a transformer, is used, is shown. If the half-wave rectified current is used, there is a disadvantage in that half of the current cannot be used, and, accordingly, energy efficient is decreased, and charging time, ranging from time T4 to T5, is increased, but there is an advantage in that a rectification circuit can be simply implemented and used when a charge/discharge frequency is not very high and the power of a required magnetic field pulse is low.

FIG. 8 illustrates an embodiment in which current $I_0$, full-wave rectified by a bridge diode (BD), is used as power. In this case, there is an advantage in that a capacitor can be charged at a higher frequency even using low power and energy efficiency is high.

The diode D0 or the bridge diode used in FIG. 7 or 8 also functions to protect the power source Vs from a reverse current, which may be induced to the primary side of the transformer along the current flow of the secondary side of the transformer and may flow in a direction opposite to that shown in the drawing, or surge current, in addition to a rectification function. Therefore, such a reverse current prevention function should be considered to be a type of rectification described in the present invention in a broad sense.

It is apparent that, even in the embodiment of FIG. 8, a current limiting means can be attached to the primary side of the transformer.

Figure 9:
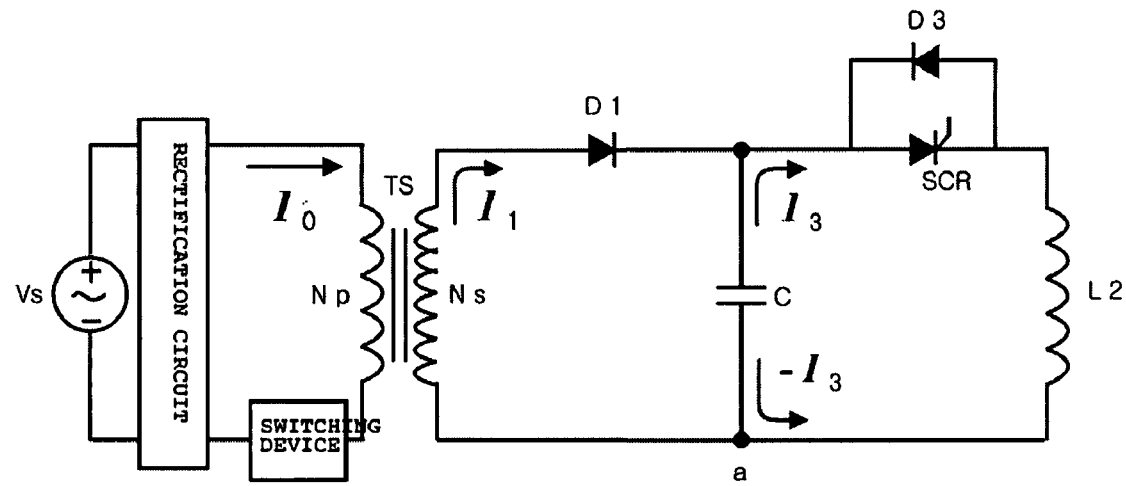
FIGS. 9 and 10 are a circuit diagram and an operating waveform diagram of another embodiment of the present invention, respectively, in which a fly-back power supply mode is used.
Figure 10:
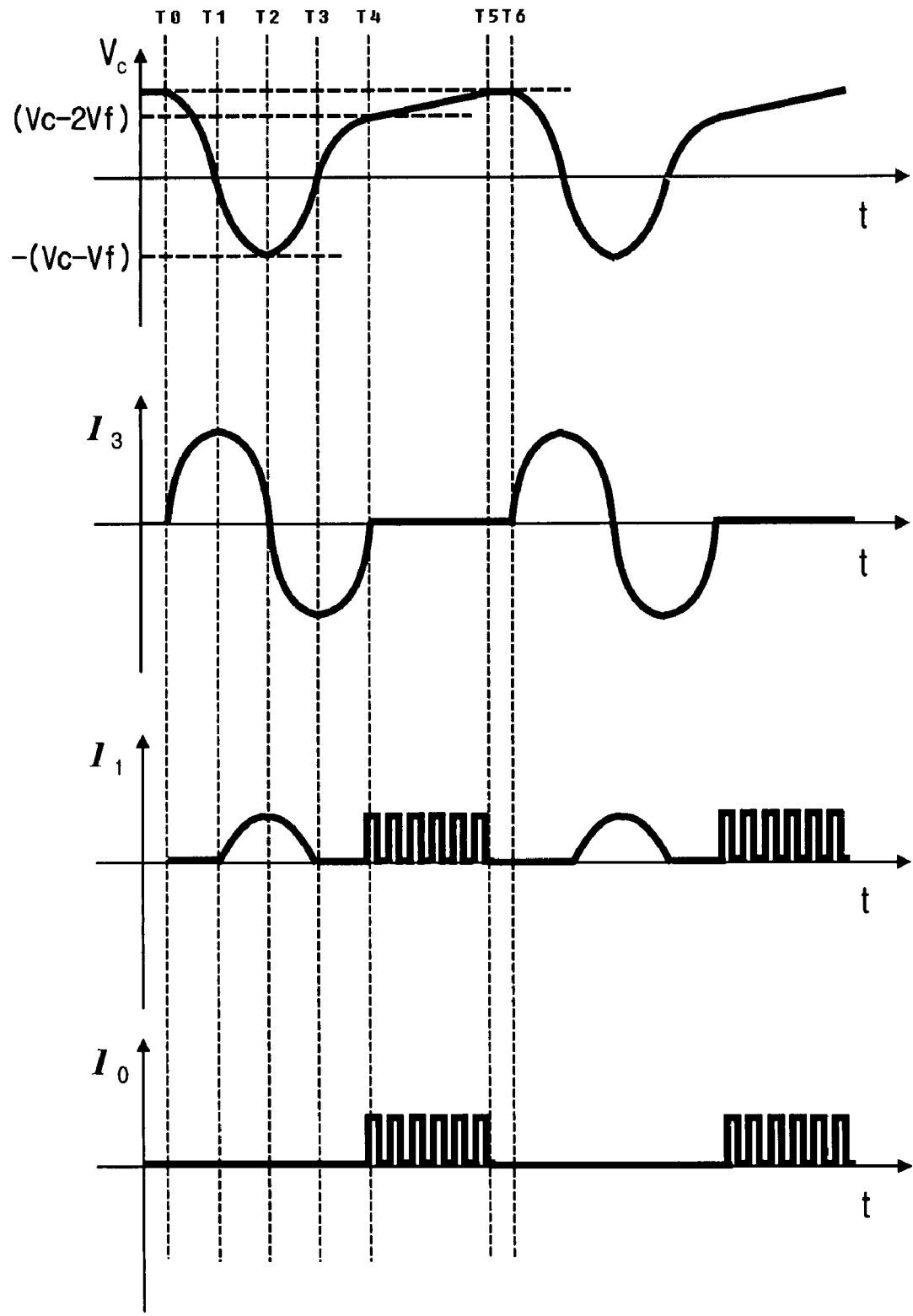

FIGS. 9 and 10 are circuit diagrams showing a circuit of supplying power in a fly-back mode according to other embodiments of the present invention.

As well-known in the art, the supply of power in a fly-back mode is a Switched-Mode Power Supply (SMPS) method, which is operated so that, if a power supply unit supplies relatively low power to an inductor on the primary side of a transformer connected to the power supply unit, and turns off a switch in the center of the circuit to interrupt the supply of power, induced power is generated at the secondary side inductor of the transformer by the energy stored in the primary side inductor of the transformer, and the induced power is supplied to the output terminal of the secondary side of the transformer. In this case, since the primary side circuit of the transformer has already been turned off, the entire power induced at the secondary side inductor of the transformer will be supplied to the output terminal, regardless of the type of reactance which devices existing on the output terminal have. Therefore, there is an advantage in that certain power can be stably supplied.

Consequently, the fly-back mode is a method of implementing a high voltage or a high current at the output terminal using relatively low power.

The circuit of FIG. 9 is designed to implement such a fly-back power supply mode and is constructed so that a switching device is disposed between the primary side of a transformer and a power supply unit. Further, the switching device on the primary side of the transformer repeatedly performs on/off operations at short periods during the above-described interval ranging from T4 to T5, which is the power supply interval, so as to supply power in the fly-back mode.

Referring to FIG. 10, showing the operating waveform of FIG. 9, to describe the above operation in detail, if the supply current $I_0$ of the primary side of the transformer is composed of a plurality of pulse waves having a short period in response to the on/off control of the switching device, the secondary side current $I_1$ induced at the secondary side inductor of the transformer is also generated in the form of pulse waves having the same period, because of the current $I_0$. Further, since the secondary side current is stored in a capacitor, and the primary side of the transformer is turned off by the switching device at each storage time, all energies induced at the secondary side inductor are stored only in the capacitor. That is, all energies are transmitted regardless of the quantity of electric charge stored in the capacitor. Therefore, this embodiment is advantageous in that the high power necessary for the present invention can be easily obtained using fly-back principles.

Figure 11:
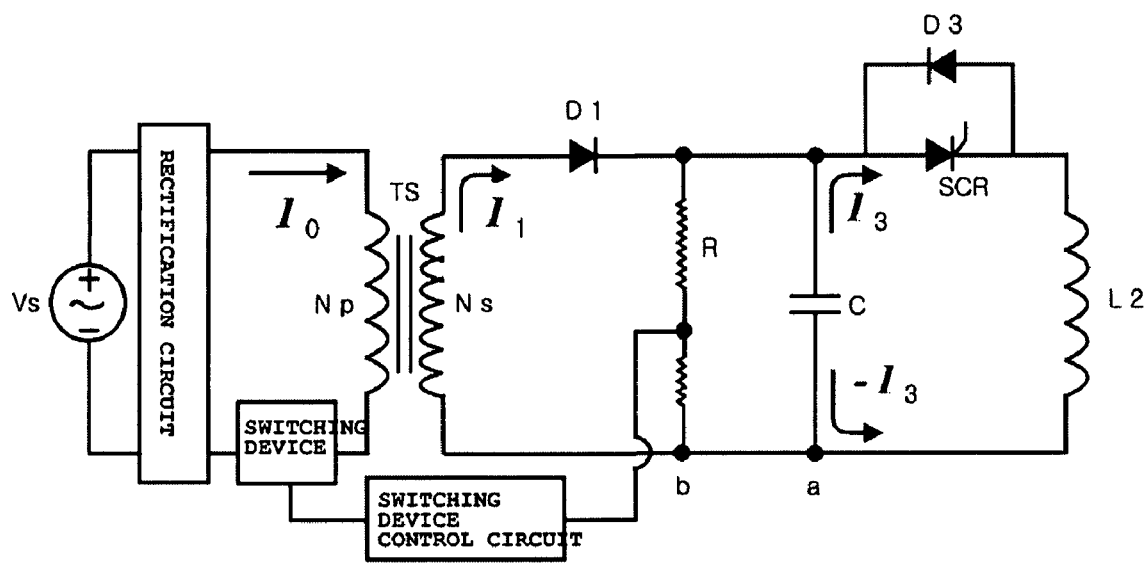
FIG. 11 is a circuit diagram showing a further embodiment of the present invention for feedback controlling a first switching means.

FIG. 11 illustrates another embodiment of the present invention, which shows the case where, when power is supplied to a capacitor by a power source in a Switched-Mode Power Supply (SMPS) mode, a switching device is controlled by a switching device control circuit for receiving the feedback of the voltage at the capacitor until the voltage at the capacitor reaches a suitable voltage Vc.

This embodiment is advantageous in that it is possible to supply power in a more precise fly-back mode by controlling the on/off operation of a switching device in real time depending on the quantity of electric charge in the capacitor.

The switching device may be controlled using a timer or counter instead of the feedback control, but it must be considered that such a feedback circuit is more precise and stable than the timer or counter. However, the present invention also includes the case where the switching device is controlled using a timer, counter or similar device, instead of the feedback circuit, as another embodiment.

As the switching device formed on the primary side of the transformer of the present invention, a Metal Oxide Semiconductor Field-Effect Transistor (MOSFET), a bipolar transistor, an Insulated Gate Bi-polar Transistor (IGBT), an Intelligent Power Module (IPM), a Gate Turn Off (GTO) thyristor, etc. can be used.

Figure 12:
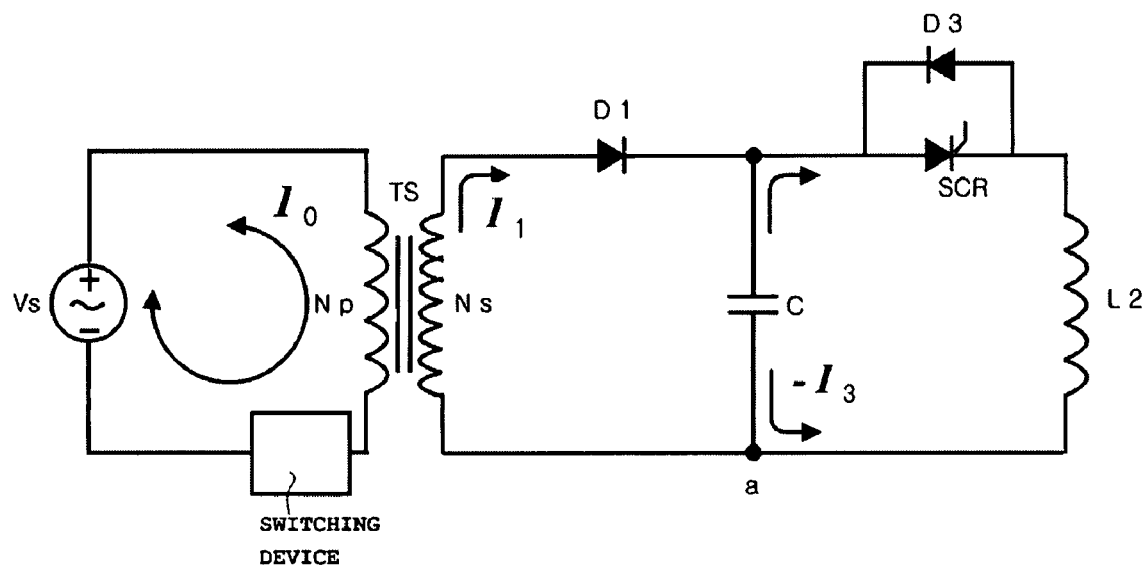
FIG. 12 is a circuit diagram showing still another embodiment of the present invention, in which a switching device, instead of a rectification circuit, is included on the primary side of a transformer.

FIG. 12 illustrates still another embodiment of the present invention, which shows the case where a rectification circuit does not exist on the primary side of a transformer. The operations of the remaining circuit parts are substantially the same as those of the above embodiments.

If a rectification circuit does not exist on the primary side of the transformer, AC power is supplied to the transformer. The reason for supplying the AC power in this way is that a rectified voltage can be always transferred to a capacitor because a diode D1 exists on the secondary side of the transformer. In this case, the diode D1 may be designated as a rectification/reverse flow prevention means existing on the secondary side of the transformer.

In this embodiment, power can be supplied in either a forward mode or a fly-back mode.

In the case of the forward mode, a switching device connected in series with the primary side of the transformer performs only the function of controlling overcurrent that may flow through the primary side of the transformer. That is, in order to prevent an induced current, which is induced from the secondary side of the transformer and may flow through the primary side of the transformer, from influencing a power supply unit when L-C resonance occurs or the capacitor is discharged, the primary side path of the transformer is turned off using the switching device existing on the primary side of the transformer. The off-state of the switching device replaces the above-described power protection function using the rectification circuit.

In the case of the supply of power in a fly-back mode, the switching device also functions to protect the above-described power supply unit on the primary side of the transformer while being used as a fly-back switch. That is, the switching device is used to store charges in a capacitor while being repeatedly turned on or off during the supply of power, and is turned off to prevent overcurrent from flowing into the power supply unit on the primary side of the transformer during the discharging of the capacitor or L-C resonance.

Figure 13:
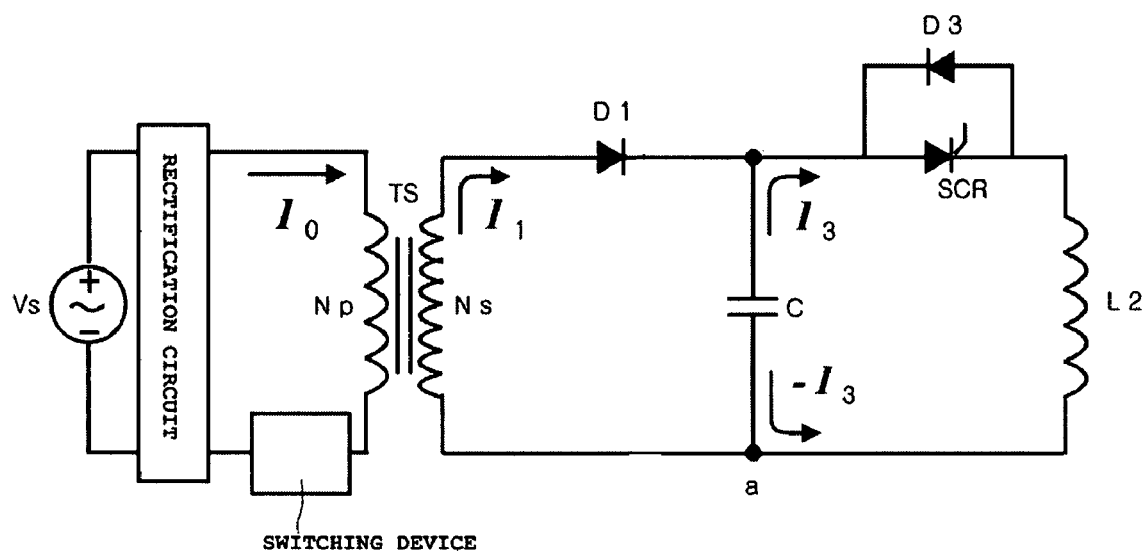
FIG. 13 is a circuit diagram showing still another embodiment of the present invention, in which a rectification circuit and a switching means are arranged on the primary side of a transformer.

FIG. 13 illustrates still another embodiment of the present invention, in which both a rectification circuit and a switching device are placed on the primary side of a transformer, and which is identical to that of FIG. 9.

In the circuit of FIG. 13, the switching device is used as a switching means for supplying power in a fly-back mode, and also performs the function of preventing a reverse current that may flow through the primary side of the transformer. Therefore, this embodiment is characterized in that the rectification circuit on the primary side of the transformer is used only as a means for supplying DC current, and the function of preventing overcurrent from flowing through the primary side during L-C resonance is performed by turning off the switching device.

The reason for requiring this construction is to completely break a circuit because a reverse current, which may flow through the primary side of the transformer during resonance, is excessively high, it is impossible to prevent overcurrent using only the rectification circuit constructed on the primary side, and breakdown may occur, so that a power supply can be destroyed or damaged.

Those skilled in the art, understanding the technical characteristics of the present invention, will easily design various circuits modified from the above embodiments of the present invention.

For example, a rectification function can be performed using only a single diode or bridge circuit existing on the primary or secondary side of the transformer. Therefore, the rectification circuit described in the present invention is not necessarily provided on the primary side of the transformer, but a rectification circuit existing on the secondary side of the transformer can be implemented. Further, even when a switching device is placed on the primary side of the transformer, current can be supplied in a simple forward mode or half-bridge mode. In this case, the switching device performs only the function of preventing a reverse current from flowing through the primary side of the transformer.

Further, as the switching device and the rectification circuit of the present invention, any well-known devices can be used, so that they are not limited to the shown devices.

Further, instead of the SCR, other switching means for performing a similar function can be used.

The invention claimed is:

1. An electric circuit, comprising:
a power supply unit;
rectification means for rectifying current from the power supply unit;
a transformer having an inductor on a primary side thereof connected to the power supply unit through the rectification means;
a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof;
reverse flow prevention means connected in series between the capacitor and the transformer to prevent charges stored in the capacitor from reversely flowing toward the transformer when the power is supplied;
a discharge inductor for receiving the charges stored in the capacitor as discharge current and forming a magnetic field;
first switching means for turning on or off flow of the discharge current that flows in one direction from the capacitor to the discharge inductor; and
bypass means for causing current to flow in one direction from the discharge inductor to the capacitor,
wherein the discharge current can cause L-C resonance between the discharge inductor and the capacitor through the first switching means and the bypass means,
wherein, if the discharge current generates a magnetic field in the discharge inductor while causing L-C resonance, the power supply unit compensates the capacitor for power, lost due to the generation of the magnetic field, through the transformer,
wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and
wherein the rectification means prevents a reverse current that may flow from the primary side inductor of the transformer to the power supply unit during L-C resonance.

2. The electric circuit according to claim 1, further comprising second switching means connected in series between the power supply unit and the primary side of the transformer.

3. The electric circuit according to claim 1, wherein the rectification means is implemented using at least one of a diode for half-wave rectification and a bridge diode for full-wave rectification.

4. The electric circuit according to claim 1, wherein the secondary side inductor of the transformer includes a core having a saturation value sufficient to prevent the core from being magnetically saturated by current flowing through the secondary side of the transformer at least during the L-C resonance.

5. The electric circuit according to claim 1, wherein the secondary side inductor of the transformer has an inductance that is 10 to 1000 times that of the discharge inductor.

6. The electric circuit according to claim 2, further comprising control means for receiving feedback of a voltage at the capacitor to provide a signal required to control on/off of the second switching means.

7. The electric circuit according to claim 2, wherein the second switching means controls on/off of a path connected from the primary side inductor of the transformer to the power supply unit so that power is supplied in any one of a fly-back mode and a forward mode when the power supply unit supplies power to the capacitor.

8. The electric circuit according to claim 2, wherein the second switching means includes any one type of device of a Metal Oxide Semiconductor Field-Effect Transistor (MOSFET), a bipolar transistor, an Insulated Gate Bi-polar Transistor (IGBT), an Intelligent Power Module (IPM), and a Gate Turn Off (GTO) thyristor.

9. The electric circuit according to claim 1, further comprising current limiting means connected between the power supply unit and the primary side of the transformer.

10. A magnetic stimulator, the magnetic stimulator comprising a power supply unit, a circuit unit supplied with power from the power supply unit to generate a magnetic field, and a control unit for controlling the circuit unit, the magnetic stimulator generating a magnetic field required for medical treatment, wherein the circuit unit comprises:
rectification means for rectifying current from the power supply unit;

a transformer having an inductor on a primary side thereof connected to the power supply unit through the rectification means;
a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof;
reverse flow prevention means connected in series between the capacitor and the transformer to prevent charges stored in the capacitor from reversely flowing toward the transformer when the power is supplied;
a discharge inductor for receiving the charges stored in the capacitor as discharge current and forming a magnetic field;
first switching means for turning on or off flow of the discharge current that flows in one direction from the capacitor to the discharge inductor; and
bypass means for causing current to flow in one direction from the discharge inductor to the capacitor,
wherein the discharge current can cause L-C resonance between the discharge inductor and the capacitor through the first switching means and the bypass means,
wherein, if the discharge current generates a magnetic field in the discharge inductor while causing L-C resonance, the power supply unit compensates the capacitor for power, lost due to the generation of the magnetic field, through the transformer,
wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance,
wherein the rectification means prevents a reverse current that may flow from the primary side inductor of the transformer to the power supply unit during L-C resonance, and
wherein, if a magnetic field is generated in the discharge inductor by the L-C resonance, the magnetic field is penetrated into an affected part of a patient, thus generating an induced current in the affected part.

11. The magnetic stimulator according to claim 10, further comprising second switching means connected in series between the power supply unit and the transformer.

12. The magnetic stimulator according to claim 10, wherein the secondary side inductor of the transformer includes a core having a saturation value sufficient to prevent the core from being magnetically saturated by current flowing through the secondary side of the transformer at least during the L-C resonance.

13. The magnetic stimulator according to claim 10, wherein the secondary side inductor of the transformer has an inductance that is 10 to 1000 times that of the discharge inductor.

14. The magnetic stimulator according to claim 10, wherein the rectification means is implemented using at least one of a diode for half-wave rectification and a bridge diode for full-wave rectification.

15. The magnetic stimulator according to claim 11, further comprising control means for receiving feedback of a voltage at the capacitor to provide a signal required to control on/off of the second switching means.

16. The magnetic stimulator according to claim 11, wherein the second switching means includes any one type of device of a Metal Oxide Semiconductor Field-Effect Transistor (MOSFET), a bipolar transistor, an Insulated Gate Bipolar Transistor (IGBT), an Intelligent Power Module (IPM), and a Gate Turn Off (GTO) thyristor.

17. The magnetic stimulator according to claim 11, wherein the second switching means controls on/off of a path connected from the primary side inductor of the transformer to the power supply unit so that power is supplied in any one of a fly-back mode and a forward mode when the power supply unit supplies power to the capacitor.

18. The magnetic stimulator according to claim 10, further comprising current limiting means connected between the power supply unit and the primary side of the transformer.

19. An electric circuit, comprising:
a power supply unit;
rectification means for rectifying current from the power supply unit;
a transformer having an inductor on a primary side thereof connected to the power supply unit through the rectification means;
a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof;
reverse flow prevention means connected in series between the capacitor and the transformer to prevent charges stored in the capacitor from reversely flowing toward the transformer when the power is supplied;
a discharge inductor for receiving the charges stored in the capacitor as discharge current and forming a magnetic field;
first switching means for turning on or off flow of the discharge current that flows in one direction from the capacitor to the discharge inductor;
bypass means for causing current to flow in one direction from the discharge inductor to the capacitor; and
second switching means connected in series between the power supply unit and the transformer,
wherein the discharge current can cause L-C resonance between the discharge inductor and the capacitor through the first switching means and the bypass means,
wherein, if the discharge current generates a magnetic field in the discharge inductor while causing L-C resonance, the power supply unit compensates the capacitor for power, lost due to the generation of the magnetic field, through the transformer,
wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and
wherein the second switching means controls on/off of a path connected from the primary side inductor of the transformer to the power supply unit so that power can be supplied in a fly-back mode when the power supply unit supplies power to the capacitor, and
wherein the rectification means prevents a reverse current that may flow from the primary side inductor of the transformer to the power supply unit during L-C resonance.

20. The electric circuit according to claim 19, wherein the second switching means prevents a reverse current that may flow from the primary side inductor to the power supply unit, together with the rectification means.

21. The electric circuit according to claim 19, wherein the rectification means is implemented using at least one of a diode for half-wave rectification and a bridge diode for full-wave rectification.

22. The electric circuit according to claim 19, wherein the secondary side inductor of the transformer includes a core having a saturation value sufficient to prevent the core from being magnetically saturated by current flowing through the secondary side of the transformer at least during the L-C resonance.

23. The electric circuit according to claim 19, wherein the secondary side inductor of the transformer has an inductance that is 10 to 1000 times that of the discharge inductor.

24. The electric circuit according to claim 19, further comprising control means for receiving feedback of a voltage at the capacitor to provide a signal required to control on/off of the second switching means.

25. The electric circuit according to claim 19, wherein the second switching means includes any one type of device of a Metal Oxide Semiconductor Field-Effect Transistor (MOSFET), a bipolar transistor, an Insulated Gate Bi-polar Transistor (IGBT), an Intelligent Power Module (IPM), and a Gate Turn Off (GTO) thyristor.

26. A magnetic stimulator, the magnetic stimulator comprising a power supply unit, a circuit unit supplied with power from the power supply unit to generate a magnetic field, and a control unit for controlling the circuit unit, the magnetic stimulator generating a magnetic field required for medical treatment, wherein the circuit unit comprises:
    rectification means for rectifying current from the power supply unit;
    a transformer having an inductor on a primary side thereof connected to the power supply unit through the rectification means;
    a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof;
    reverse flow prevention means connected in series between the capacitor and the transformer to prevent charges stored in the capacitor from reversely flowing toward the transformer when the power is supplied;
    a discharge inductor for receiving the charges stored in the capacitor as discharge current and forming a magnetic field;
    first switching means for turning on or off flow of the discharge current that flows in one direction from the capacitor to the discharge inductor;
    bypass means for causing current to flow in one direction from the discharge inductor to the capacitor; and
    second switching means connected in series between the power supply unit and the transformer,
    wherein the discharge current can cause L-C resonance between the discharge inductor and the capacitor through the first switching means and the bypass means,
    wherein, if the discharge current generates a magnetic field in the discharge inductor while causing L-C resonance, the power supply unit compensates the capacitor for power, lost due to the generation of the magnetic field, through the transformer,
    wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and
    wherein the second switching means controls on/off of a path connected from the primary side inductor of the transformer to the power supply unit so that power can be supplied in a fly-back mode when the power supply unit supplies power to the capacitor,
    wherein the rectification means prevents a reverse current that may flow from the primary side inductor of the transformer to the power supply unit during L-C resonance, and
    wherein, if a magnetic field is generated in the discharge inductor by the L-C resonance, the magnetic field is penetrated into an affected part of a patient, thus generating an induced current in the affected part.

27. The magnetic stimulator according to claim 26, wherein the secondary side inductor of the transformer includes a core having a saturation value sufficient to prevent the core from being magnetically saturated by current flowing through the secondary side of the transformer at least during the L-C resonance.

28. The magnetic stimulator according to claim 26, wherein the secondary side inductor of the transformer has an inductance that is 10 to 1000 times that of the discharge inductor.

29. The magnetic stimulator according to claim 26, wherein the rectification means is implemented using at least one of a diode for half-wave rectification and a bridge diode for full-wave rectification.

30. The magnetic stimulator according to claim 26, further comprising control means for receiving feedback of a voltage at the capacitor to provide a signal required to control on/off of the second switching means.

31. The magnetic stimulator according to claim 26, wherein the second switching means includes any one type of device of a Metal Oxide Semiconductor Field-Effect Transistor (MOSFET), a bipolar transistor, an Insulated Gate Bi-polar Transistor (IGBT), an Intelligent Power Module (IPM), and a Gate Turn Off (GTO) thyristor.

32. An electric circuit, comprising:
    a power supply unit;
    a transformer having an inductor on a primary side thereof connected to the power supply unit;
    a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof;
    rectification/reverse flow prevention means connected in series between the capacitor and the transformer to simultaneously supply Direct Current (DC) current to the capacitor and prevent charges stored in the capacitor from reversely flowing toward the transformer when the power is supplied;
    a discharge inductor for receiving the charges stored in the capacitor as discharge current and forming a magnetic field;
    first switching means for turning on or off flow of the discharge current that flows from the capacitor to the discharge inductor;
    bypass means for causing current to flow in one direction from the discharge inductor to the capacitor; and second switching means connected in series between the power supply unit and the transformer, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, and wherein the second switching means controls on/off of a path connected from the primary side inductor of the transformer to the power supply unit so that power can be supplied in a fly-back mode when the power supply unit supplies power to the capacitor, and, in addition, the second switching means is turned off during L-C resonance to prevent a reverse current that may flow from the primary side inductor of the transformer to the power supply unit.

33. The electric circuit according to claim 32, wherein the secondary side inductor of the transformer includes a core having a saturation value sufficient to prevent the core from being magnetically saturated by current flowing through the secondary side of the transformer at least during the L-C resonance.

34. The electric circuit according to claim 32, wherein the secondary side inductor of the transformer has an inductance that is 10 to 1000 times that of the discharge inductor.

35. A magnetic stimulator, the magnetic stimulator comprising a power supply unit, a circuit unit supplied with power from the power supply unit to generate a magnetic field, and a control unit for controlling the circuit unit, the magnetic stimulator generating a magnetic field required for medical treatment, wherein the circuit unit comprises:

a transformer having an inductor on a primary side thereof connected to the power supply unit;

a capacitor connected to an inductor on a secondary side of the transformer corresponding to the inductor on the primary side of the transformer, and operated so that, if power is supplied by the power supply unit through the primary side inductor of the transformer, the capacitor is supplied with the power from the secondary side of the transformer and stores charges at both ends thereof;

rectification/reverse flow prevention means connected in series between the capacitor and the transformer to simultaneously supply Direct Current (DC) current to the capacitor and prevent charges stored in the capacitor from reversely flowing toward the transformer when the power is supplied;

a discharge inductor for receiving the charges stored in the capacitor as discharge current and forming a magnetic field;

first switching means for turning on or off flow of the discharge current that flows from the capacitor to the discharge inductor;

bypass means for causing current to flow in one direction from the discharge inductor to the capacitor; and second switching means connected in series between the power supply unit and the transformer, wherein the discharge current can cause L-C resonance between the discharge inductor and the capacitor through the first switching means and the bypass means, wherein, if the discharge current generates a magnetic field in the discharge inductor while causing L-C resonance, the power supply unit compensates the capacitor for power, lost due to the generation of the magnetic field, through the transformer, wherein the secondary side inductor of the transformer has a relatively higher inductance than that of the discharge inductor, and is used as power supply means during supply of power to the capacitor, and is used as a buffer inductor for attenuating current flowing through the secondary side of the transformer during L-C resonance, wherein the second switching means controls on/off of a path connected from the primary side inductor of the transformer to the power supply unit so that power can be supplied in a fly-back mode when the power supply unit supplies power to the capacitor, and, in addition, the second switching means is turned off during L-C resonance to prevent a reverse current that may flow from the primary side inductor of the transformer to the power supply unit, and wherein, if a magnetic field is generated in the discharge inductor by the L-C resonance, the magnetic field is penetrated into an affected part of a patient, thus generating an induced current in the affected part.

36. The magnetic stimulator according to claim 35, wherein the secondary side inductor of the transformer includes a core having a saturation value sufficient to prevent the core from being magnetically saturated by current flowing through the secondary side of the transformer at least during the L-C resonance.

37. The magnetic stimulator according to claim 35, wherein the secondary side inductor of the transformer has an inductance that is 10 to 1000 times that of the discharge inductor.

* * * * *